(12) United States Patent
Colston, Jr. et al.

(10) Patent No.: US 9,422,586 B2
(45) Date of Patent: Aug. 23, 2016

(54) METHOD FOR GENETIC IDENTIFICATION OF UNKNOWN ORGANISMS

(75) Inventors: Billy W. Colston, Jr., San Ramon, CA (US); Joseph P. Fitch, Livermore, CA (US); Benjamin J. Hindson, Livermore, CA (US); J. Chance Carter, Livermore, CA (US); Neil Reginald Beer, Pleasanton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 2401 days.

(21) Appl. No.: 11/818,623

(22) Filed: Jun. 15, 2007

(65) Prior Publication Data

US 2010/0055677 A1   Mar. 4, 2010

(51) Int. Cl.
| | |
|---|---|
| C12M 1/00 | (2006.01) |
| C12M 1/34 | (2006.01) |
| C12M 1/36 | (2006.01) |
| C12M 3/00 | (2006.01) |
| C12Q 1/04 | (2006.01) |
| B01L 3/00 | (2006.01) |
| C12Q 1/68 | (2006.01) |
| G01N 33/543 | (2006.01) |
| G01N 33/569 | (2006.01) |
| G01N 33/58 | (2006.01) |
| B01L 7/00 | (2006.01) |

(52) U.S. Cl.
CPC ............ C12Q 1/04 (2013.01); B01L 3/502761 (2013.01); B01L 3/502784 (2013.01); C12Q 1/6888 (2013.01); G01N 33/5432 (2013.01); G01N 33/569 (2013.01); G01N 33/587 (2013.01); B01L 7/52 (2013.01); B01L 2200/0673 (2013.01); B01L 2200/10 (2013.01); B01L 2300/087 (2013.01); B01L 2300/0816 (2013.01); B01L 2300/0864 (2013.01); B01L 2300/0867 (2013.01); B01L 2400/0487 (2013.01)

(58) Field of Classification Search
None
See application file for complete search history.

(56) References Cited

U.S. PATENT DOCUMENTS

| | | | |
|---|---|---|---|
| 6,924,094 B1 | 8/2005 | Gingeras et al. | |
| 7,010,391 B2 | 3/2006 | Handique et al. | |
| 7,041,481 B2 | 5/2006 | Anderson et al. | |
| 7,462,469 B2 * | 12/2008 | Bass et al. | 435/91.2 |

OTHER PUBLICATIONS

Williams, R., et al., "Amplification of complex gene libraries by emulsion PCR," Nature Methods, vol. 3, No. 7, Jul. 2006, pp. 545-550.
Diehl, F., et al., "BEAMing: single-molecule PCR on microparticles in waterin-oil emulsions," Nature Methods, vol. 3, No. 7, Jul. 2006, pp. 551-559.
Joanicot, M., et al., "Droplet Control for Microfluidics," Science, vol. 309, Aug. 5, 2005, pp. 887-888.

(Continued)

*Primary Examiner* — Ja'na Hines
(74) *Attorney, Agent, or Firm* — Eddie E. Scott

(57) ABSTRACT

A method of rapid, genome and proteome based identification of unknown pathogenic or non-pathogenic organisms in a complex sample. The entire sample is analyzed by creating millions of emulsion encapsulated microdroplets, each containing a single pathogenic or non-pathogenic organism sized particle and appropriate reagents for amplification. Following amplification, the amplified product is analyzed.

5 Claims, 9 Drawing Sheets

(56) References Cited

OTHER PUBLICATIONS

Ksiazek, T.G., et al., "A Novel Coronavirus Associated with Severe Acute Respiratory Syndrome," The New England Journal of Medicine, vol. 348, No. 20, May 15, 2003, 16 pgs.

Musyanpovych, A., et al., "Miniemulsion Droplets as Single Molecule Nanoreactors for Polymerase Chain Reaction," Biomacromolecules 2005, 6, pp. 1824-1828.

Leamon, J.H., et al., "Overview: methods and applications for droplet copartmentalization of biology," Nature Methods, vol. 3, No. 7, Jul. 2006, pp. 541-543.

He, M., et al., "Selective Encapsulation of Single Cells and Subcellular Organelles into Picoliter- and Femtoliter—Volume Droplets," Analytical Chemistry, -cont'd-.

vol. 77, No. 6, Mar. 15, 2005, pp. 1539-1544.

Nakano, M., et al., "Single-molecule PCR using water-in-oil emulsion," Journal of Biotechnology, 102, 2003, pp. 117-124.

\* cited by examiner

METHOD FOR GENETIC IDENTIFICATION OF UNKNOWN ORGANISMS

The United States Government has rights in this invention pursuant to Contract No. W-7405-ENG-48 between the United States Department of Energy and the University of California for the operation of Lawrence Livermore National Laboratory.

CROSS-REFERENCE TO RELATED APPLICATIONS

This application is related to U.S. patent application Ser. No. 11/650,363 filed Jan. 4, 2007 by Neil Reginald Beer, Benjamin J. Hindson, Billy W. Colston, Jr., and Joseph Patrick Fitch; titled, "Sorting, Amplification, Detection, and Identification of Nucleic Acid Subsequences in a Complex Mixture," assigned to the Regents of the University of California, the same assignee as this application. U.S. patent application Ser. No. 11/650,363 titled, "Sorting, Amplification, Detection, and Identification of Nucleic Acid Subsequences in a Complex Mixture" filed Jan. 4, 2007 by Neil Reginald Beer, Benjamin J. Hindson, Billy W. Colston, Jr., and Joseph Patrick Fitch is incorporated herein by this reference.

BACKGROUND

1. Field of Endeavor

The present invention relates to pathogen identification and more particularly to a method for genetic identification of unknown pathogenic or non-pathogenic organisms in a sample.

2. State of Technology

U.S. Pat. No. 6,924,094 issued Aug. 2, 2005 for chip-based species identification and phenotypic characterization of microorganisms invented by Thomas R. Gingeras, David Mack, Mark S. Chee, Anthony J. Berno, Lubert Stryer, Ghassan Ghandour, and Ching Wang provides state of technology information. U.S. Pat. No. 6,924,094 discloses systems, methods, and devices for characterizing and identifying organisms. In one aspect it provides, a method for identifying a genotype of a first organism, comprising: (a) providing an array of oligonucleotides at known locations on a substrate, said array comprising probes complementary to reference DNA or RNA sequences from a second organism; (b) hybridizing a target nucleic acid sequence from the first organism to the array; and (c) based on an overall hybridization pattern of the target to the array, identifying the genotype of the first organism, and optionally identifying a phenotype of the first organism.

U.S. Pat. No. 7,010,391 for methods and systems for control of microfluidic devices invented by Kalyan Handique, Karthik Ganesan, and Sundaresh N. Brahmasandra provides state of technology information. U.S. Pat. No. 7,010,391 discloses a method for controlling the operation of a digital-type microfluidic ("MF") device (i) wherein an MF device includes one or more passages for confining one or more micro-droplets, the passages having one or more stable positions for the micro-droplets, and (ii) includes one or more internal components responsive to control signals, the internal components operatively associated with the passages for control and monitoring the MF device, the method including: (a) providing one or more micro-droplet processing requests, wherein a micro-droplet processing request specifies performing at least one action on at least one micro-droplet, the requests including either (i) creating one or more new micro-droplets at selected stable positions, or (ii) moving one or more micro-droplets from current stable positions to selected next stable positions, or (iii) combining two or more micro-droplets into one or more new micro-droplets at selected stable positions, or (iv) mixing one or more micro-droplets, and (b) generating control signals, which are provided to the MF device, wherein the control signals are generated in a pattern and sequence that is responsive to each micro-droplet processing request so that the internal components of the MF device that are responsive to the control signals function together to perform the requested micro-droplet processing in the MF device.

U.S. Pat. No. 7,041,481 for chemical amplification based on fluid partitioning invented by Brian L. Anderson, Billy W. Colston, Jr., and Chris Elkin provides state of technology information. U.S. Pat. No. 7,041,481 discloses an apparatus for nucleic acid amplification of a sample comprising means for partitioning the sample into partitioned sections and means for performing PCR on the partitioned sections of the sample. Another embodiment of the invention provides an apparatus for nucleic acid amplification and detection of a sample comprising means for partitioning the sample into partitioned sections, means for performing PCR on the partitioned sections of the sample, and means for detection and analysis of the partitioned sections of the sample. The present invention also provides a method of nucleic acid amplification of a sample comprising the steps of partitioning the sample into partitioned sections and subjecting the partitioned sections of the sample to PCR. Another embodiment of a method of the present invention provides a method of nucleic acid amplification and detection of a sample comprising the steps of partitioning the sample into partitioned sections, subjecting the partitioned sections of the sample to PCR, and detecting and analyzing the partitioned sections of the sample.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The Achilles heel of the nation's biodefense is identification of unknown or emerging threats. Identification of unknown or rapidly evolving viruses remains a significant challenge. There are an estimated $10^{31}$ viruses on earth. Most viruses are impossible to culture, making traditional phenotypic characterization infeasible. Current detection approaches are inadequate for several important classes of biological threats including: known, but rapidly evolving threat pathogens [e.g., highly pathogenic avian influenza (HPAI)]; continuously emerging pathogens (e.g., SARS); genetically modified traditional agents; and advanced biological warfare (ABW) agents. Without the ability to rapidly identify and characterize a previously unknown or emerging pathogen, a timely and effective response is highly unlikely.

The need to reduce the time required to respond to infectious diseases is a growing concern among scientists and health-care experts. Infectious disease epidemics are potentially the most lethal and certainly most insidious of natural disasters. Bubonic plague (*Yersinia pestis*) was responsible for a staggering 25 million deaths (roughly a quarter of the entire population) in 14th century Europe. Although less deadly than the plague, smallpox was a universal scourge of humanity for thousands of years, and had a tremendous impact on the development of Western civilization. In 1918 a global pandemic caused by an unusual strain of Spanish influenza killed more than 50 million people in the span of 8 months and hospitalized more individuals than the total number of those wounded in World War I.

Since the development of antibiotic and vaccine therapies in the early 1900's, mortality from infectious disease dropped considerably. Smallpox was declared officially "eradicated" by the World Health Organization in 1977, save for secured repositories of the variola major virus in two international research laboratories. Other diseases such as plague, measles and polio were similarly conquered. In recent years, however, the U.S. death rate from infectious disease has begun to rise again. Influenza and pneumonia remain among the top ten causes of death for all age classes in the United States. New infectious diseases pose serious threats to public health, while strategies to combat these pathogens are being investigated. West Nile virus, which broke out in Romania in 1996 and Russia in 1999, has recently spread throughout most of the United States. Perhaps the most devastating infectious disease that humanity has faced since smallpox and bubonic plague, Acquired Immune Deficiency Syndrome (AIDS) has struck 60 million individuals worldwide. Five million new cases of HIV infection were reported in 2001, with 3 million deaths and 40 million individuals living with HIV/AIDS.

In recent years, we have seen more deadly pathogens emerge from nature such as Ebola virus the causative agent of Hemorrhagic fever. Furthermore, existing pathogens are becoming much more virulent and less sensitive to existing treatments and genetic engineering techniques now enable the creation of potentially more deadly pathogens. One key delay in responding to these threats is the ability to rapidly isolate and genetically identify an unknown pathogen from a complex clinical or environmental sample. Currently available DNA-sequencing techniques, such as those used in the recent SARS response, allow analysis of newly discovered pathogens. These techniques, however, rely on early identification and isolation of the pathogen from complex and often diluted samples (ref. 5). Therefore samples with very large viral or bacterial loads are needed or the target agent must be cultured through multiple steps using growth patterns for isolation and amplification. There are human pathogens that are not amenable to culture.

It is well known that quarantine strategies are much more difficult and costly to implement once a disease has spread. Therefore, effective response to a terrorist attack using a pathogen similar in virulence and contagion to the 1918 flu will require surveillance and characterization 10 to 100 times more rapid than was accomplished in the outstanding and unprecedented international response to SARS.

The present invention provides an apparatus and method for identifying pathogenic and non-pathogenic organisms in a sample. The method includes preparing the sample, isolating the organism from the sample into microdroplets, sorting the microdroplets, analyzing the microdroplets, and classifying and identifying the organisms. The apparatus includes structural elements for preparing the sample, isolating the organism from the sample into microdroplets, sorting the microdroplets, analyzing the microdroplets, and classifying and identifying the organisms.

The present invention has many uses. For example the present invention can be used in clinical applications for identification of unknown respiratory illnesses, unknown causes of death, drug efficacy testing, and other identification. The present invention can be used in medical surveillance for identification of new and emerging infectious disease such as SARS. The present invention can be used for identification of genetically modified biological threats. The present invention can also be used for identification of environmental biological background characterization for planning, response, forensics, and attribution.

One embodiment of the present invention provides a method for performing rapid genome and proteome identification of unknown pathogenic or non-pathogenic organisms in a complex sample. The entire sample is analyzed by creating an ordered emulsion consisting of millions of aqueous droplets in an immiscible fluid. The droplets are typically monodisperse, microns in diameter, with tunable volumes ranging from picoliters to nanoliters. Mineral oil and perfluorinated hydrocarbons are examples of water immiscible fluids compatible with biological assays and are well suited to this application. The microdroplets each contain a single pathogenic or non-pathogenic organism sized particle and the appropriate reagents for conducting an assay. The microdroplets can be tracked from the point at which they were formed through all the subsequent steps until all analysis steps are complete. Once encapsulated within a droplet, the organisms can be lysed to release nucleic acids, making them accessible to amplification reagents. After lysis, the single droplet can be split into multiple droplets, to enable parallel interrogation of their genomic and proteomic contents. The assays conducted on the droplets may include an amplification step, to generate copies of the target, and or to amplify the signal for detection. Following amplification, the amplified product is analyzed. Amplification can be used to generate copies of nucleic acids or proteins by reverse transcription polymerase chain reaction (RT-PCR), in vitro translation, respectively, or other amplification techniques. The analysis can be by sequencing, separation, spectrometry, spectroscopy, electrochemistry and other analysis techniques.

The underlying principle of the method is that a single organism, such as a virus particle, is encapsulated in its own discrete microdroplet. Each organism is comprised of a multitude of analytes, including nucleic acids and proteins and other molecules. The microdroplets compartmentalize all analytes from a single organism and serve as discrete reaction vessels. Assays can be conducted within each microdroplet by incorporating the appropriate reagents. The products of an assay are measured for each droplet, and the corresponding results are correlated to the individual analyte. The present invention offers single organism resolution whereas most conventional biological identification techniques measure the average properties of analytes associated with entire population of organisms present in the sample. This new capability is particularly important when the prevalence of a target organism in a sample is low, compared to the total number of closely related (or background) organisms in the sample. Using conventional techniques, the unique properties of the target organism may be masked when the analysis is conducted in bulk solution.

Microdroplets constrain assay products to extremely small volumes, thereby avoiding dilution. The higher concentrations of products generated in the microdroplets increase the probability of detection. By contrast, if the same assay was conducted in bulk solution the concentration of product may be below the detection limit of a given detector. Constraining the analyte and reagents in a very small geometry also speeds reaction kinetics, leading to faster detection. Discrete single particle resolution is important for characterizing each individual organism within the entire population of organisms within a whole sample. This is important for determining virulence, drug resistance, mapping evolutionary changes including rates of change, types, probabilities and frequency of mutations.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
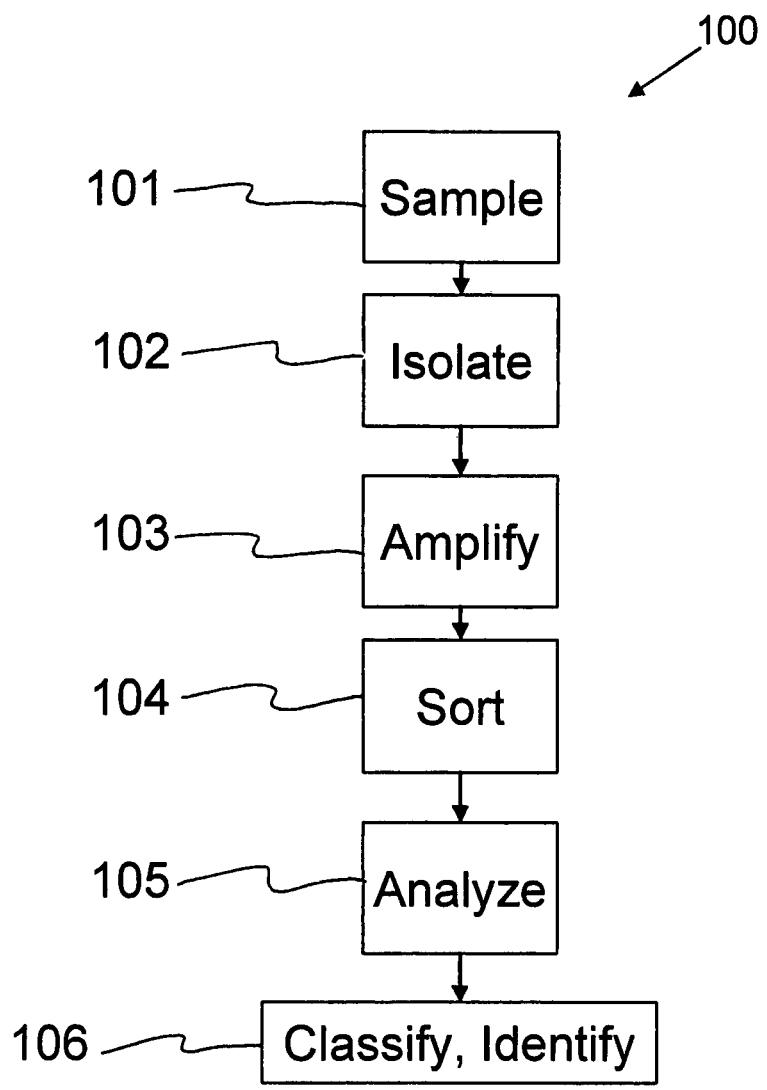
FIG. 1 illustrates one embodiment of a method of identifying all of the unknown pathogenic or non-pathogenic organisms in a sample.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to the drawings and in particular to FIG. 1, one embodiment of a method of identifying all of the pathogenic and non-pathogenic organisms in a sample wherein the organisms include nucleic acids and proteins in accordance with the present invention is illustrated. The Merriam-Webster dictionary defines "organism" as: a complex structure of interdependent and subordinate elements whose relations and properties are largely determined by their function in the whole. The term organism includes viruses, bacteria, protozoa, microbes, and other pathogenic or non-pathogenic entities.

The method is designated generally by the reference numeral 100. The method 100 identifies substantially all of the pathogenic and non-pathogenic organisms in the sample. The method 100 does not rely on isolation or culturing of a novel pathogen which can take weeks to accomplish, but instead allows rapid, parallel genetic and proteomic profiling of nearly every individual microbe present in a given complex sample.

The method 100 includes the steps of acquiring and preparing the sample 101, isolating 102 each organism into a microdroplet, performing amplification 103 of either targets and or signals in a microdroplet, sorting the droplets 104, analyzing the droplets and their contents 105 and then analyzing the results to classify and identify 106 all organisms in the sample. The method arranges the organisms for parallel analysis, and analyzes all of the pathogenic and non-pathogenic organisms in the sample.

First, the sample 101 must be acquired. The sample could be biological material of human, animal or plant origin in addition to other materials generated in the laboratory such as cell cultures. Clinical samples may include saliva, whole blood, plasma, tissue, and others. Samples may also be collected from the environment including aerosols, soil, water, and others.

Second, the sample must be isolated 102 into microdroplets. Isolation incorporates many steps including sample preparation, droplet generation, reagent addition, and droplet splitting. Referring to sample preparation, biological assays, including the PCR, often require a number of sample preparation steps be conducted to remove any interfering molecules or particles from the sample matrix prior to conducting subsequent assays. Sample preparation may include chemical treatment, dilution, buffer exchange, separation, cytometry, filtration, or concentration. The degree of sample preparation required will be dependent on the sample matrix and the assay to be used. Some samples may require very little or no sample preparation. Other sample types may require preparation steps including homogenization (grinding of tissue, bead beating, mixing), digestion (enzymatic, thermal, chemical), lysis and others. Once prepared, the sample can be loaded onto the device for droplet generation. Referring to droplet generation, droplets are created by forcing the aqueous sample stream through an appropriately sized mechanical orifice where it merges with an immiscible fluid. This may be accomplished using microfluidic, microjet, inkjet, pin systems, or other ways of creating droplets. Water immiscible fluids such as mineral oil and fluorinated hydrocarbons are compatible with many biological assays and can be used to generate stable aqueous microdroplets in an immiscible fluid. The diameter and volume of each droplet can be adjusted by varying physical (flow rate, orifice sizes, temperature, surface tension, and viscosity) or chemical (polarity, surface chemistry) parameters or both. Referring to reagent addition, assay reagents can be mixed with the sample prior to sample loading and droplet generation. Alternatively, assay reagents can be added in-line either prior to, during, or after microdroplet generation via microfluidic junctions (Y or T or X junctions), or via the direct injection of reagents to each droplet. Alternatively, separate reagents droplets can be merged with sample droplets at any point during the analysis. The properties of the assay reagents may affect the formation (size, volume) and stability of droplets (coalescence). Additives (surfactants, lipids, glycerol, polymers, etc.) can be used to control the formation and stability of the microdroplets and their contents. Referring to droplet splitting, the microdroplets can be split into smaller droplets to generate identical fractions of the sample. Splitting of the microdroplets may be done at any stage during the process. For example, after sample preparation and droplet generation, droplets can be split to generate sub-droplets which can proceed to parallel analysis trains (e.g., genomic and proteomic).

Third, the sample encapsulated within each droplet is amplified 103. Amplification assays conducted in the microdroplets can be designed to target a single class of analyte (single-plex) or multiple analytes simultaneously (multiplex). The amplification assays can be of tunable specificity using specific primers with different levels of discrimination, or random primers. Different types of amplification reactions can be conducted in series for each individual organism within a microdroplet. Orthogonal assays can be conducted within the same droplet when the reaction chemistries are compatible or separately. Parallel high-throughput processing can be achieved by conducting multiple different assays (singleplex or multiplex) on the same sample. The parallel analysis and accompanying instrument platform can also accommodate the processing of multiple samples simultaneously.

Fourth, droplets are sorted 104. Sorting can help to reduce the burden on the subsequent analysis steps by only allowing those droplets that contain sample or amplified sample to proceed. Those droplets that do not contain sample or did not undergo successful amplification can be discarded.

Fifth, the droplets are then analyzed 105 using a suite of analytical techniques conducted either in series or in parallel or both.

Sixth, the results of all measurements are analyzed and compiled to classify and identify 106 the organism.

Figure 2:
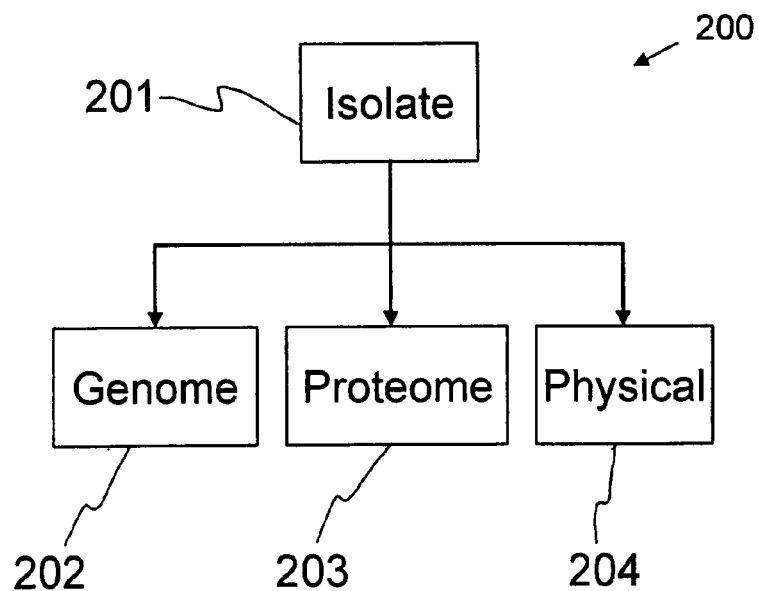
FIG. 2 illustrates an embodiment of a system for isolating all of the unknown pathogenic or non-pathogenic organisms in a sample.

FIG. 2 illustrates a system for isolating all of the unknown pathogenic or non-pathogenic organisms in a sample. The system is designated generally by the reference numeral 200. The samples are isolated 201 based on the type of analysis to be performed including genomic 202, proteomic 203, and physical 204 analysis. Isolation incorporates all the necessary steps that need to prepare a raw sample for amplification, including sample preparation, droplet generation, reagent addition, and droplet splitting. At this isolate step, droplet tracking can begin by monitoring spatial coordinates for each droplet, or by monitoring a unique signature of each droplet. The signature used for tracking droplets may be inherent to the contents of the droplet or be incorporated via the addition of a unique identifier to each droplet, such as a barcode. The tracking signature is preserved when a droplet is split into sub-droplets. Tracking of each droplet from the isolate step to the completion of the analysis step will allow for the compilation, integration, analysis and interpretation of all data sets gathered on each droplet encapsulated organism.

During the isolate step 201, the analytes (e.g., nucleic acids or proteins) can been released from the organisms, referred to as lysis. Lysis can be performed in-line on each droplet encapsulating a single organism. The lysis step disrupts the structures of the organism including, for example, cell walls, lipid membranes, protein coats, or capsids thereby releasing the analytes making them accessible for amplification. A number of approaches can be used to lyse an organism in a microdroplet, including electromagnetic (laser light), chemical, acoustic (ultrasound), enzymatic (proteases), thermal (including heating and cooling) and others. Lysis can be performed as part of the step of preparing the sample, or after the step of creating droplets from the sample, or both. Other preparation steps can be achieved within each droplet. A combination of lysis techniques can be used at different steps in the process to release analytes selectively. A droplet encapsulating the contents of a single organism can be split to enable parallel analysis (e.g., genetic, proteomic and physical analysis on a single virus particle or cell). Alternatively, the analysis can be conducted on the same droplet sequentially, where compatibility of the assay chemistries permits and the integrity of the analytes can be preserved between analyses. For example, proteins will be denatured during thermal cycling but nucleic acids may remain intact during protein synthesis.

Figure 3:
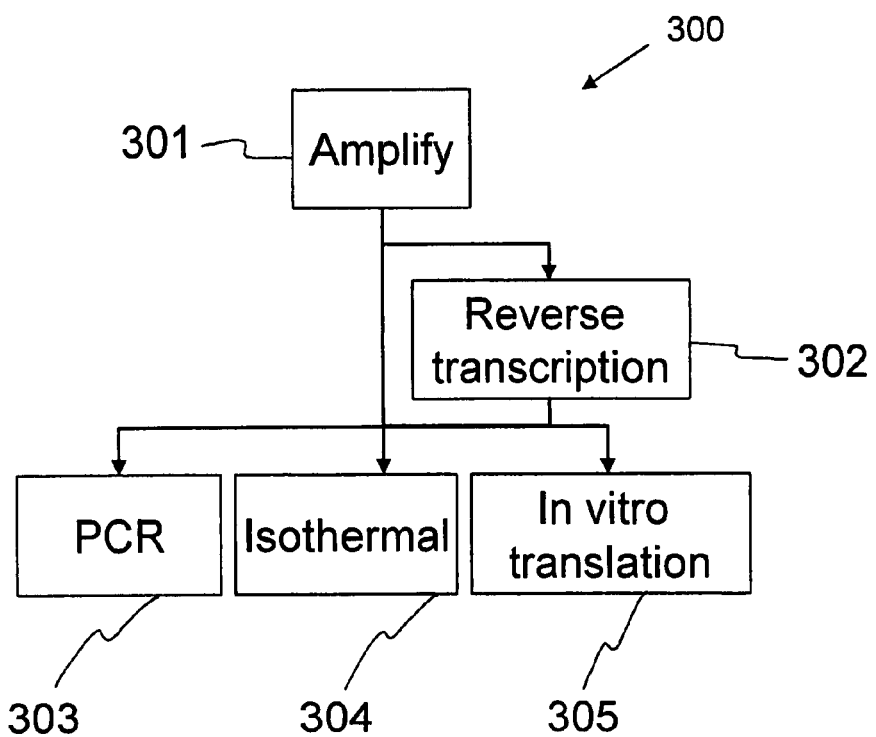
FIG. 3 illustrates one embodiment of a system for amplifying genomic and proteomic targets.

FIG. 3 shows one embodiment of a system for amplifying genomic and proteomic targets. The system is designated generally by the reference numeral 300. The system 300 includes the following modules: amplify 301, reverse transcription 302, PCR 303, isothermal 304, and in vitro translation 305.

For genomic analysis, amplification of RNA can be achieved by reverse-transcription using an RNA polymerase, to yield cDNA. cDNA can be analyzed directly or amplified further using a thermal stable polymerase via the PCR. PCR amplifies genomic or cDNA and requires the use of a thermocycler. Isothermal amplification refers to enzyme-based methods that can also be performed to amplify nucleic acids including genomic DNA and cDNA. By definition, isothermal amplification occurs at a single temperature and does not require a thermocycler. Isothermal amplification can include both reverse transcription and DNA amplification steps, either as a one-step or two-step protocol. Proteomic analysis may require protein synthesis. Protein synthesis can be achieved using in vitro translation (IVT) methods whereby the starting material can be RNA, circular DNA, linear DNA (plasmid) or PCR product. IVT can be performed concurrently, or after nucleic acid amplification depending on the starting material. Proteomic analysis can be used to identify gene products, conduct protein folding studies, and determine protein function.

Amplification 301 can be performed in highly parallel fluidic channels (stopped flow, flow-through) or using 1-D, 2-D or 3-D arrays. Signal amplification can also be incorporated as part of the target amplification step. Signal amplification relies on the multiplication of the response parameter, using for example enzymatic (e.g., luminescence), spectroscopic (e.g., SERS), or chemical (e.g., silver deposition on gold-nanoparticles) approaches.

Figure 4:
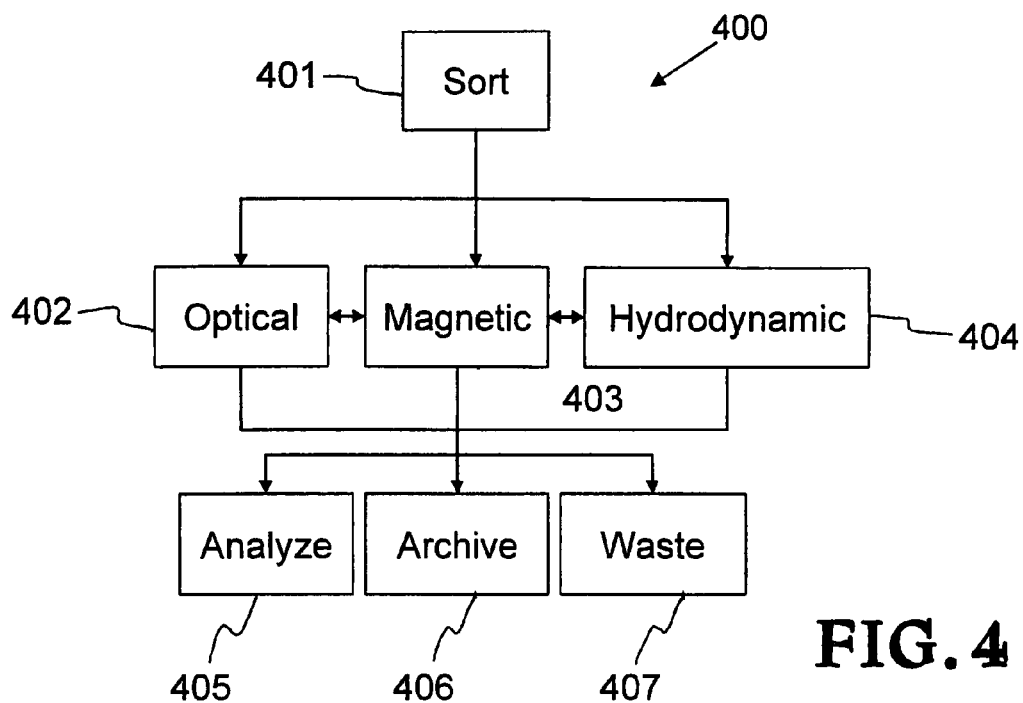
FIG. 4 illustrates an embodiment of an apparatus for sorting microdroplets.

FIG. 4 shows an embodiment of an apparatus for sorting microdroplets. The system is designated generally by the reference numeral 400. The system 400 includes the following modules: sort 40100, optical 402, magnetic 403, hydrodynamic 404, analyze 405, archive 406, and waste 407.

Sorting identifies, and then collects the fraction of droplets containing a target organism that underwent successful amplification. Depending on the concentration of the organism in the sample, the size of the droplets and the efficiency of the amplification steps, many droplets may not have amplified. As a result, a fraction of the droplets may be discarded to waste, or stored in a droplet archive for retrieval and follow-up analysis if required. Sorting may reduce the burden on the detection system by presenting only a fraction of the total droplets for analysis (step 105). Sorting can be achieved using optical, hydrodynamic, and magnetic mechanisms or most likely a combination thereof. Sorting can be conducted within a fluidic channel. Sorting on a 1-D, 2-D or 3-D array can be achieved by assigning geometric coordinates to each category of droplet, followed by picking a sub-population of droplets for further analysis. Optical sorting can be based on measuring the spectroscopic properties of each droplet (e.g., luminescence, turbidity, light scattering, absorption, transmission, vibration, etc.). Optical sorting can be based on a direct spectroscopic measurement of the droplet and its contents. Alternatively, it can be an indirect measurement, whereby a specific indicator or probe was added to each droplet (e.g., a dsDNA intercalating fluorescence probe, labeled nano-particles to indicate successful PCR amplification, labeled antibody). Sorting can be non-invasive so as not to disrupt the microdroplets. Magnetic sorting can be achieved by incorporation of inert or labeled paramagnetic nano-particles to each droplet followed by application of an external magnetic field. Hydrodynamic sorting can be achieved using cytometry, diffusion, and hydrodynamic focusing based approaches. A combination of pumps, valves and flow channels can be used to conduct high-throughput sorting of microdroplets in microfluidic circuitry.

Figure 5:
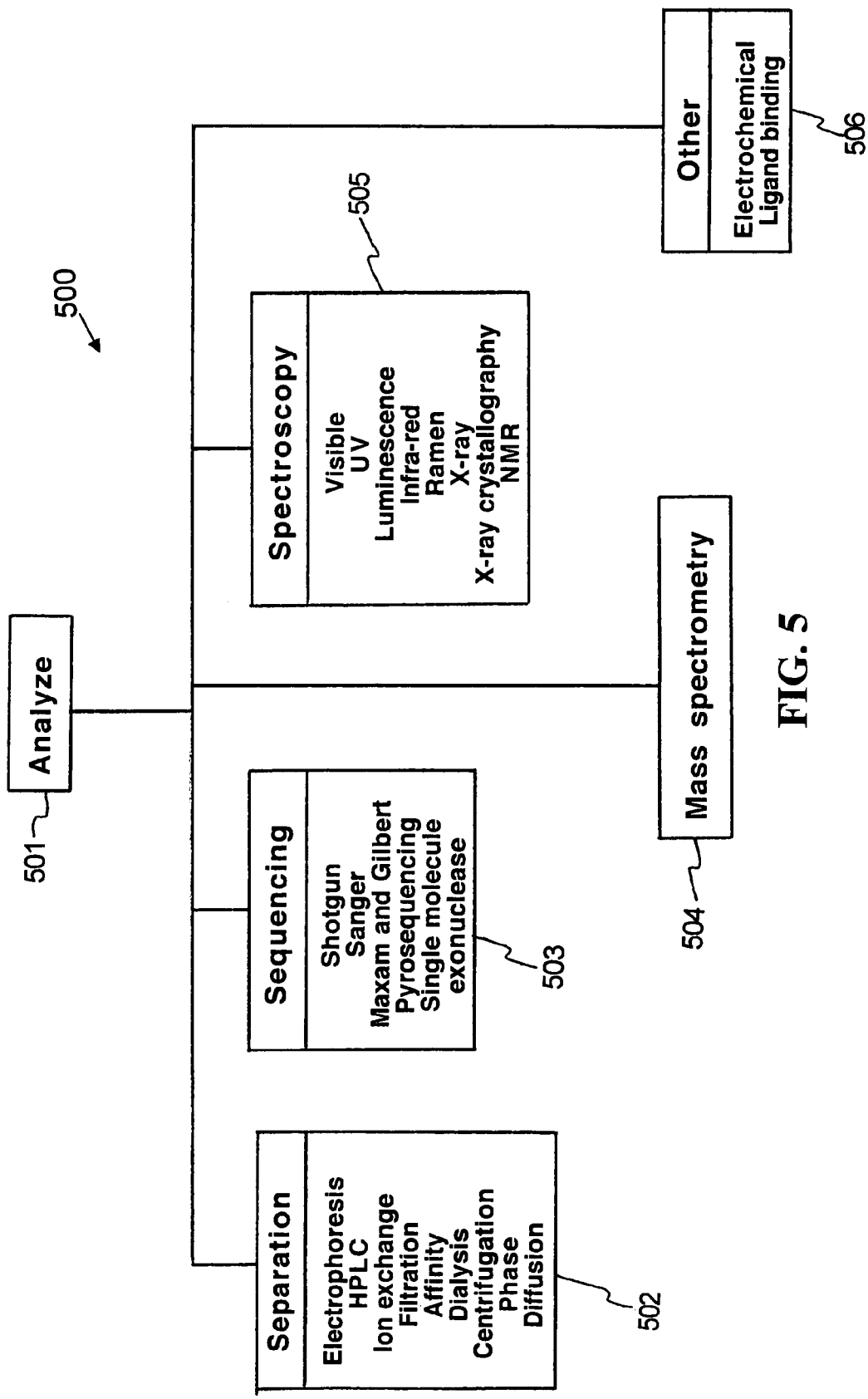
FIG. 5 illustrates an embodiment of a system of analyzing each of the droplets to identify all of the unknown pathogenic or non-pathogenic organisms in a sample.

FIG. 5 shows an embodiment of a system of analyzing each of the droplets to identify all of the unknown pathogenic or non-pathogenic organisms in a sample. The system is designated generally by the reference numeral 500. The system 500 includes the following modules: analyze 501, separation 502, sequencing 503, mass spectrometry 504, spectroscopy 505, and other 506 techniques. Separation 502 includes electrophoresis, HPLC, ion exchange, filtration, affinity, dialysis, centrifugation, phase, and diffusion. Sequencing 503 includes shotgun, Sanger, Maxam and Gilbert, pyrosequencing, single molecule, and exonuclease. Spectroscopy 505 includes visible, UV, luminescence, infra-red, raman, X-ray, X-ray crystallography, and NVR. Other 506 includes electrochemical and ligand binding.

Droplets can be formatted depending on the analysis to be performed. A suite of detection technologies can be used to interrogate the contents of each droplet. Examples include separation, sequencing, mass spectrometry, optical (spectroscopic, fluorescence, Raman, NMR, X-ray crystallography, SEM, AFM), ligand binding, and electrochemical methods. Detection systems can be arranged as modules to operate independently, in parallel, or in series. For example, a droplet may undergo separation by microchip capillary electrophoresis with fluorescence detection, peak (band) selection, followed by sequencing and matrix assisted laser desorption ionization mass spectrometry. For techniques that consume or change the composition of the sample, droplets may be split to provide aliquots of the amplified droplet material for delivery to a suite of detectors. Alternatively, droplets may be "sipped" by sub-micrometer needles or orifices that serve as the sample injection interface to a given detector.

Figure 6:
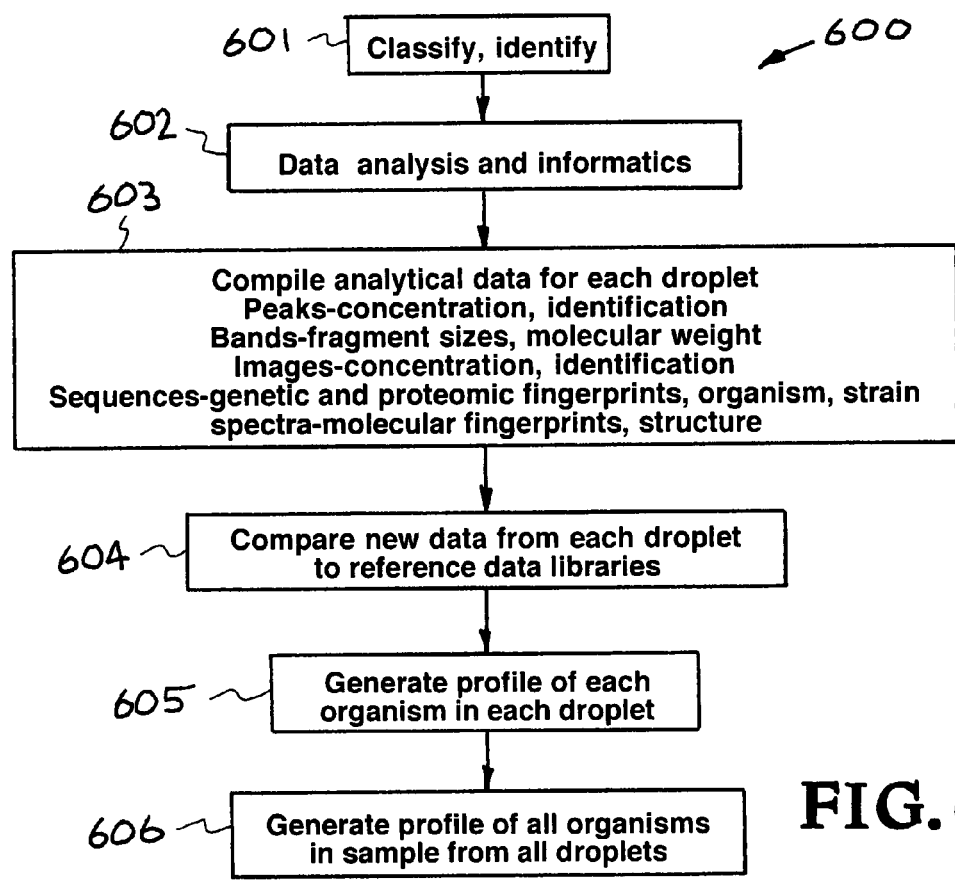
FIG. 6 represents the informatics and data analysis methods for classification and identification of the all of the unknown pathogenic or non-pathogenic organisms in a sample.

FIG. 6 shows an embodiment of the informatics and data analysis system for classification and identification of the all of the unknown pathogenic or non-pathogenic organisms in a sample. The system is designated generally by the reference numeral 600. The system 600 includes the following modules: classify and identify 601, data analysis and informatics 602, compile analytical data for each droplet 603, compare new data from each droplet to reference libraries 604, generate a profile for each organism in each droplet 605, generate a profile of all organisms in the sample from all droplets 606. The step 601 of classify and identify can be accomplished by performing data analysis and informatics 602 of detector data generated by the earlier step 501. Detector data could be in the form of peaks, bands, images, sequences, spectra and others. Detector data is analyzed and compiled 603 for each droplet to provide information on the organism including, for example, concentration, molecular weight, genetic and proteomic fingerprints, molecular fingerprints, molecular structure, size, charge, shape, viscosity, reaction rates, etc. The newly compiled data for each droplet is compared to existing data in reference libraries 604. This step may include the use of standardized templates to enable comparison between vastly different data sets. The comparison may include pattern recognition and matching, sequence alignments. Confidence intervals can be assigned to each data set based on factors such as quality of the analytical data generated during the analysis, or the degree with which the data matches to reference data in existing libraries. The next step is to generate a profile for each organism in each droplet 605. This could include taxonomic classification into taxa such as species, subspecies, genera, families, orders, classes, phyla, divisions, or kingdoms. Identification of organism strain is included in this step. A profile of all organisms in the sample is created by compiling the profiles of all droplets 606. The combined profile is used to classify and identify all organisms in the sample. New organisms can be assigned a new identifier and classification at this stage.

Figure 7:
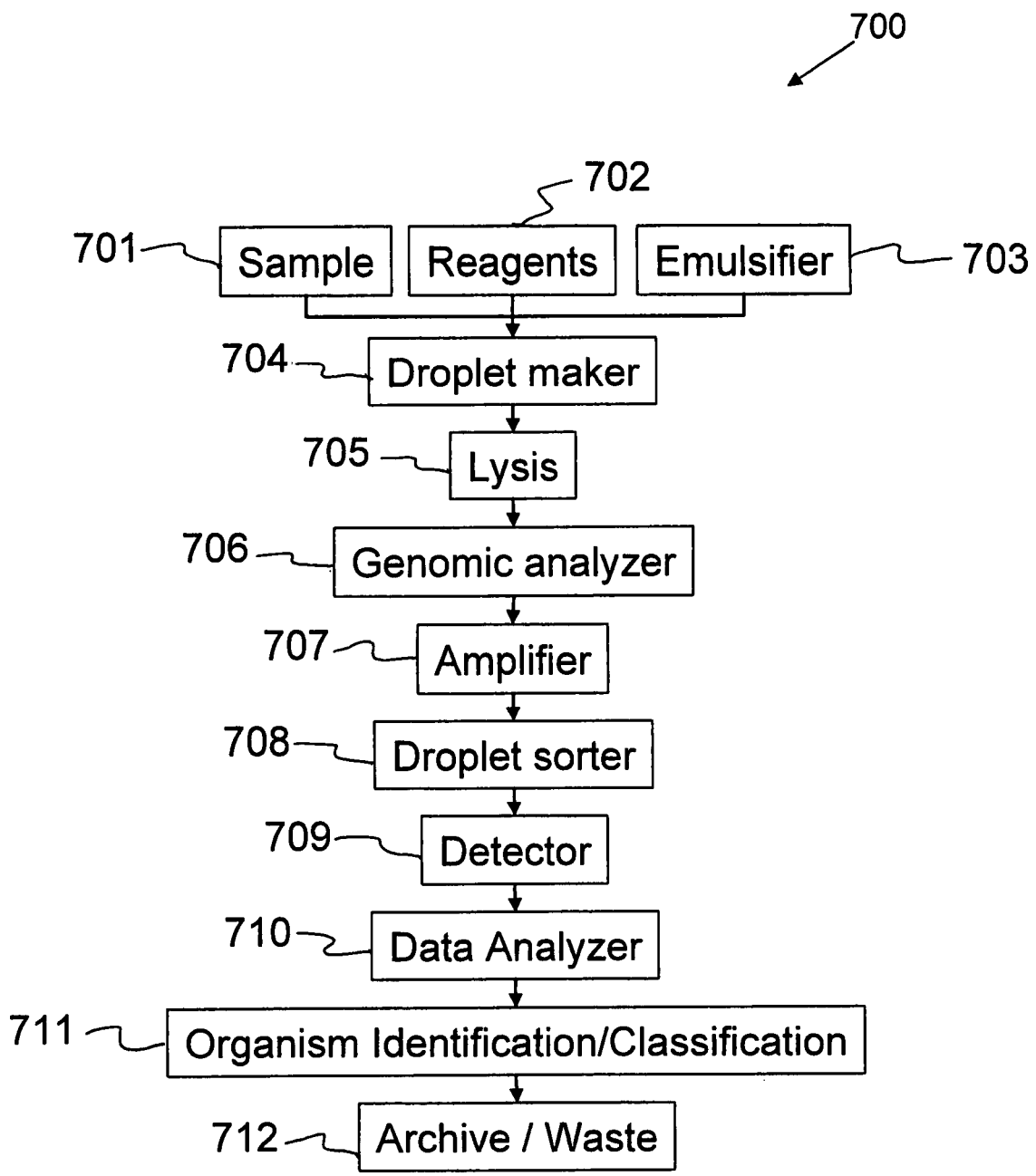
FIG. 7 illustrates an embodiment of a system for genomic identification of all of the unknown pathogenic or non-pathogenic organisms in a sample.

Referring now to FIG. 7, an embodiment of a system and apparatus for genomic identification of all of the unknown pathogenic or non-pathogenic organisms in a sample. The system is designated generally by the reference numeral 700. The system 700 identifies substantially all of the unknown pathogenic or non-pathogenic organisms in the sample 701.

As shown in FIG. 7, a sample 701 is directed into the system 700. The sample 701 contains unknown pathogenic or non-pathogenic organisms. The sample 701 is mixed with reagents 702 and an emulsifier 703. The reagents 702 may be reagents required for nucleic acid amplification including primers, probes, and dNTPs, enzymes, buffer (Tris, potassium chloride, magnesium chloride). The reagents can be added to the sample off-line or inline. Reagents can also be added using a fluidic junction mixer.

As shown in FIG. 7, the emulsifier 703 is merged with the sample 701. The portion of the system 700 wherein the sample 701, the reagents 702, and the emulsifier 703 are injected forms a droplet maker 704. The droplet maker 704 creates droplets from the sample 701 wherein the droplets constitute sub-nanoliter volume reactors containing the organism sized particles. The droplets are created by forcing an aqueous sample stream and with immiscible liquid stream through an appropriately sized mechanical orifice in the droplet maker 704. This may be accomplished using microfluidic, microjet, inkjet, pin systems, or other ways of creating droplets. Merging an aqueous sample stream with immiscible liquid within the droplet maker 704 forms the droplets containing individual organisms.

A device 705 provides lysis of the organisms to release the nucleic acids. A genomic analyzer 706 provides genomic analysis. In the genomic analysis, amplification of RNA can be achieved by reverse-transcription using an RNA polymerase to yield cDNA. cDNA can be analyzed directly or amplified further using a thermal stable polymerase via the PCR. PCR amplifies genomic or cDNA and requires the use of a thermocycler. Isothermal amplification is an enzyme-based method that can also be performed to amplify nucleic acids. By definition, isothermal amplification occurs at a single temperature and does not require a thermocycler. Isothermal amplification can include both reverse transcription and DNA amplification steps, either as a one-step or two-step protocol.

An amplifier 707 amplifies the sample 701. Amplification can be performed in highly parallel fluidic channels (stopped flow, flow-through) or using 1-D, 2-D or 3-D arrays. Signal amplification can also be incorporated as part of the target amplification step. Signal amplification relies on the multiplication of the response parameter, using for example enzymatic (e.g., luminescence), spectroscopic (e.g., SERS), or chemical (e.g., silver deposition on gold-nanoparticles) approaches.

A droplet sorter 708 sorts the droplets. Sorting identifies, and then collects the fraction of droplets containing a target organism that underwent successful amplification. Depending on the concentration of the organism in the sample, the size of the droplets and the efficiency of the amplification steps, many droplets may not have amplified. As a result, a fraction of the droplets may be discarded to waste or stored in a droplet archive as illustrated at 712. The droplet can be stored for retrieval and follow-up analysis if required. Sorting may reduce the burden on the detection system by presenting only a fraction of the total droplets for analysis. Sorting can be achieved using optical, hydrodynamic, and magnetic mechanisms or most likely a combination thereof. Sorting can be conducted within a fluidic channel. Sorting on a 1-D, 2-D or 3-D array can be achieved by assigning geometric coordinates to each category of droplet, followed by picking a sub-population of droplets for further analysis. Optical sorting can be based on measuring the spectroscopic properties of each droplet (e.g., luminescence, turbidity, light scattering, absorption, transmission, vibration, etc.). Optical sorting can be based on a direct spectroscopic measurement of the droplet and its contents. Alternatively, it can be an indirect measurement, whereby a specific indicator or probe was added to each droplet (e.g., a dsDNA intercalating fluorescence probe, labeled nano-particles to indicate successful PCR amplification, labeled antibody). Sorting can be non-invasive so as not to disrupt the microdroplets. Magnetic sorting can be achieved by incorporation of inert or labeled paramagnetic nano-particles to each droplet followed by application of an external magnetic field. Hydrodynamic sorting can be achieved using cytometry, diffusion, and focusing based approaches. A combination of pumps, valves and flow channels can be used to conduct high-throughput sorting of microdroplets.

A detector 709 provides detection of the organisms in the sample and the organisms are identified and classified at 711. The droplets may be split to provide aliquots of the amplified droplet material for delivery to a suite of detectors. The data analyzer 710 provides analysis. Analysis can be accomplished by performing informatics analysis of detector data to generate genomic and proteomic profiles for each organism sized particle in the original sample. Other physical analyses can also be performed (size, shape, pH, mobility, charge, viscosity, refractive index, kinetics, etc.). Information for each droplet is compiled, then analyzed to generate a comprehensive profile for each individual organism. The data from individual organisms can then be compiled to generate data representative of the entire population (i.e., the original sample). Data for individual organisms can be binned to produce probability density functions for each identity and classification. Confidence intervals can be assigned to each data set based on factors such as quality of the analytical data generated during the analysis, degree, or matching to existing libraries, and so on.

Figure 8:
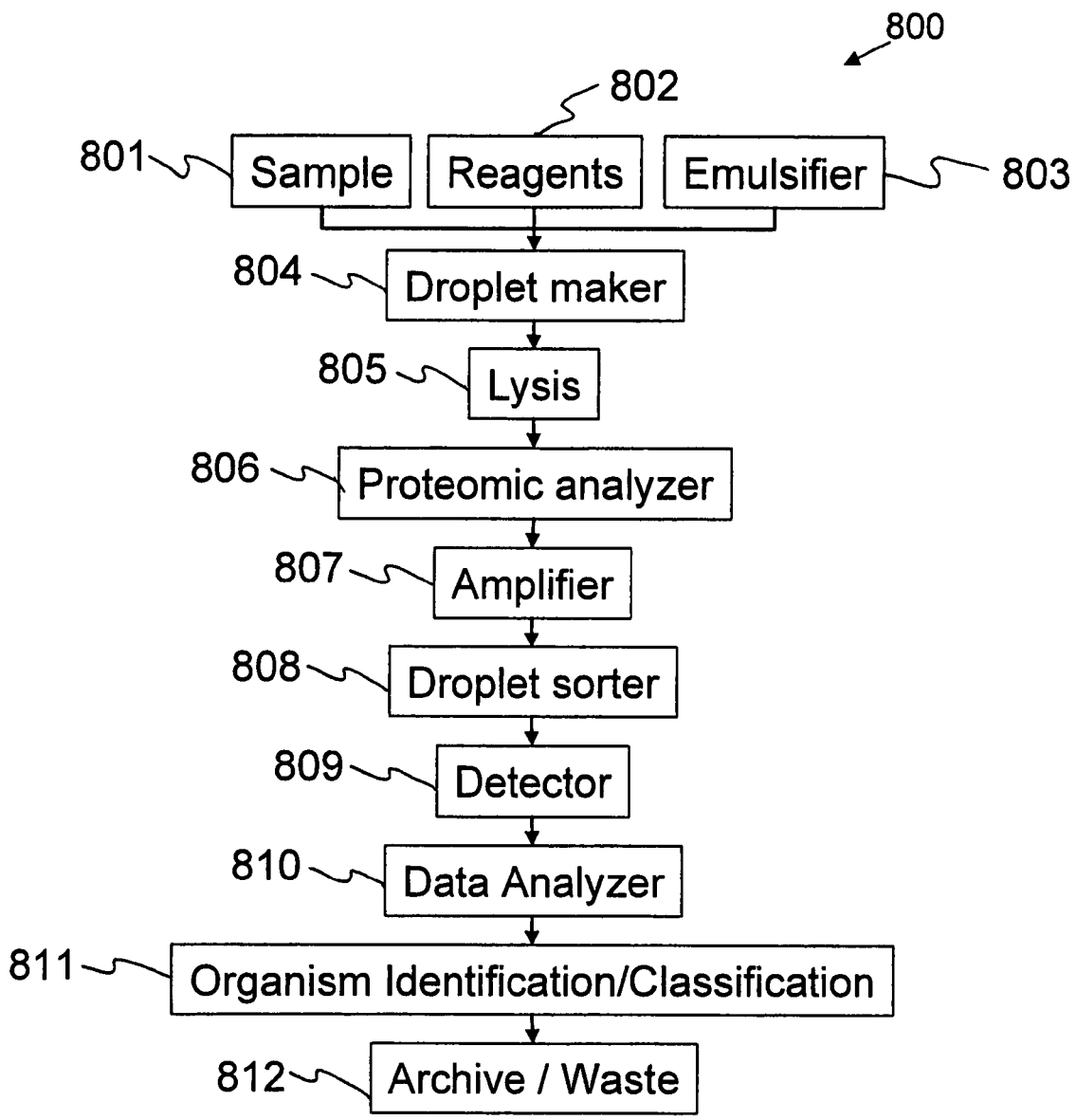
FIG. 8 illustrates yet another embodiment of a system for proteomic identification all of the unknown pathogenic or non-pathogenic organisms in a sample.

Referring now to FIG. 8, an embodiment of a system for proteomic identification of all of the unknown pathogenic or non-pathogenic organisms in a sample. The system is designated generally by the reference numeral 800. The system 800 identifies substantially all of the unknown pathogenic or non-pathogenic organisms in the sample 801.

As shown in FIG. 8, a sample 801 is directed into the system 800. The sample 801 contains unknown pathogenic or non-pathogenic organisms. The sample 801 containing the gene targets is mixed with reagents 802 and an emulsifier 803. The reagents 802 may be reagents required for protein synthesis by in vitro transcription and translation including, for example, ribosomes, tRNAs, aminoacyl-tRNA synthetases, initiation, elongation and termination factors, amino acids, energy sources (ATP, GTP), energy regenerating systems (creatine phosphate, creatine phosphokinase, phosphoenol pyruvate and pyruvate kinase), other co-factors (Mg2+, K+, etc.), primers, prokaryotic phage RNA polymerases and promoters (e.g., T7, T3, or SP6). The reagents can be added to the sample off-line or inline. Reagents can also be added using a fluidic junction mixer.

As shown in FIG. 8, the emulsifier 803 is merged with the sample 801. The portion of the system 800 wherein the sample 801, the reagents 802, and the emulsifier 803 are injected forms a droplet maker 804. The droplet maker 804 creates droplets from the sample 801 wherein the droplets constitute sub-nanoliter volume reactors containing the organism sized particles. The droplets are created by forcing an aqueous sample stream and with immiscible liquid stream through an appropriately sized mechanical orifice in the droplet maker 804. This may be accomplished using microfluidic, microjet, inkjet, pin systems, or other ways of creating droplets. Merging an aqueous sample stream with immiscible liquid within the droplet maker 804 forms the droplets containing individual organisms.

A device 806 provides lysis of the organisms to release the nucleic acids. A Proteomic analyzer 806 provides proteomic analysis. The proteomic analysis may require protein synthesis. Protein synthesis can be performed within microdroplets to identify gene products, conduct protein folding studies, and determine protein function. Protein synthesis can be achieved using in vitro translation (IVT) methods whereby the starting material can be RNA, circular DNA, linear DNA (plasmid) or PCR product. IVT can be performed concurrently, or after nucleic acid amplification depending on the starting material.

An amplifier 807 amplifies the sample 801. Amplification can be performed in highly parallel fluidic channels (stopped flow, flow-through) or using 1-D, 2-D or 3-D arrays. Signal amplification can also be incorporated as part of the target amplification step. Signal amplification relies on the multiplication of the response parameter, using for example enzymatic (e.g., luminescence), spectroscopic (e.g., SERS), or chemical (e.g., silver deposition on gold-nanoparticles) approaches.

A droplet sorter 808 sorts the droplets. Sorting identifies, and then collects the fraction of droplets containing a target organism that underwent successful amplification. Depending on the concentration of the organism in the sample, the size of the droplets and the efficiency of the amplification steps, many droplets may not have amplified. As a result, a fraction of the droplets may be discarded to waste or stored in a droplet archive as illustrated at 812. The droplet can be stored for retrieval and follow-up analysis if required. Sorting may reduce the burden on the detection system by presenting only a fraction of the total droplets for analysis. Sorting can be achieved using optical, hydrodynamic, and magnetic mechanisms or most likely a combination thereof. Sorting can be conducted within a fluidic channel. Sorting on a 1-D, 2-D or 3-D array can be achieved by assigning geometric coordinates to each category of droplet, followed by picking a sub-population of droplets for further analysis. Optical sorting can be based on measuring the spectroscopic properties of each droplet (e.g., luminescence, turbidity, light scattering, absorption, transmission, vibration, etc.). Optical sorting can be based on a direct spectroscopic measurement of the droplet and its contents. Alternatively, it can be an indirect measurement, whereby a specific indicator or probe was added to each droplet (e.g., a fluorescence probe, labeled nano-particles to indicate successful PCR amplification, labeled antibody). Sorting can be non-invasive so as not to disrupt the microdroplets. Magnetic sorting can be achieved by incorporation of inert or labeled paramagnetic nano-particles to each droplet followed by application of an external magnetic field. Hydrodynamic sorting can be achieved using cytometry, diffusion, and focusing based approaches. A combination of pumps, valves and flow channels can be used to conduct high-throughput sorting of microdroplets.

A detector 809 provides detection of the organisms in the sample and the organisms are identified and classified at 811. The droplets may be split to provide aliquots of the amplified droplet material for delivery to a suite of detectors. The data analyzer 810 provides analysis. Analysis can be accomplished by performing informatics analysis of detector data to generate genomic and proteomic profiles for each organism sized particle in the original sample. Other physical analyses can also be performed (size, shape, pH, mobility, charge, viscosity, refractive index, kinetics, etc.). Information for each droplet is compiled, then analyzed to generate a comprehensive profile for each individual organism. The data from individual organisms can then be compiled to generate data representative of the entire population (i.e., the original sample). Data for individual organisms can be binned to produce probability density functions for each identity and classification. Confidence intervals can be assigned to each data set based on factors such as quality of the analytical data generated during the analysis, degree or matching to existing libraries, and so on.

Figure 9:
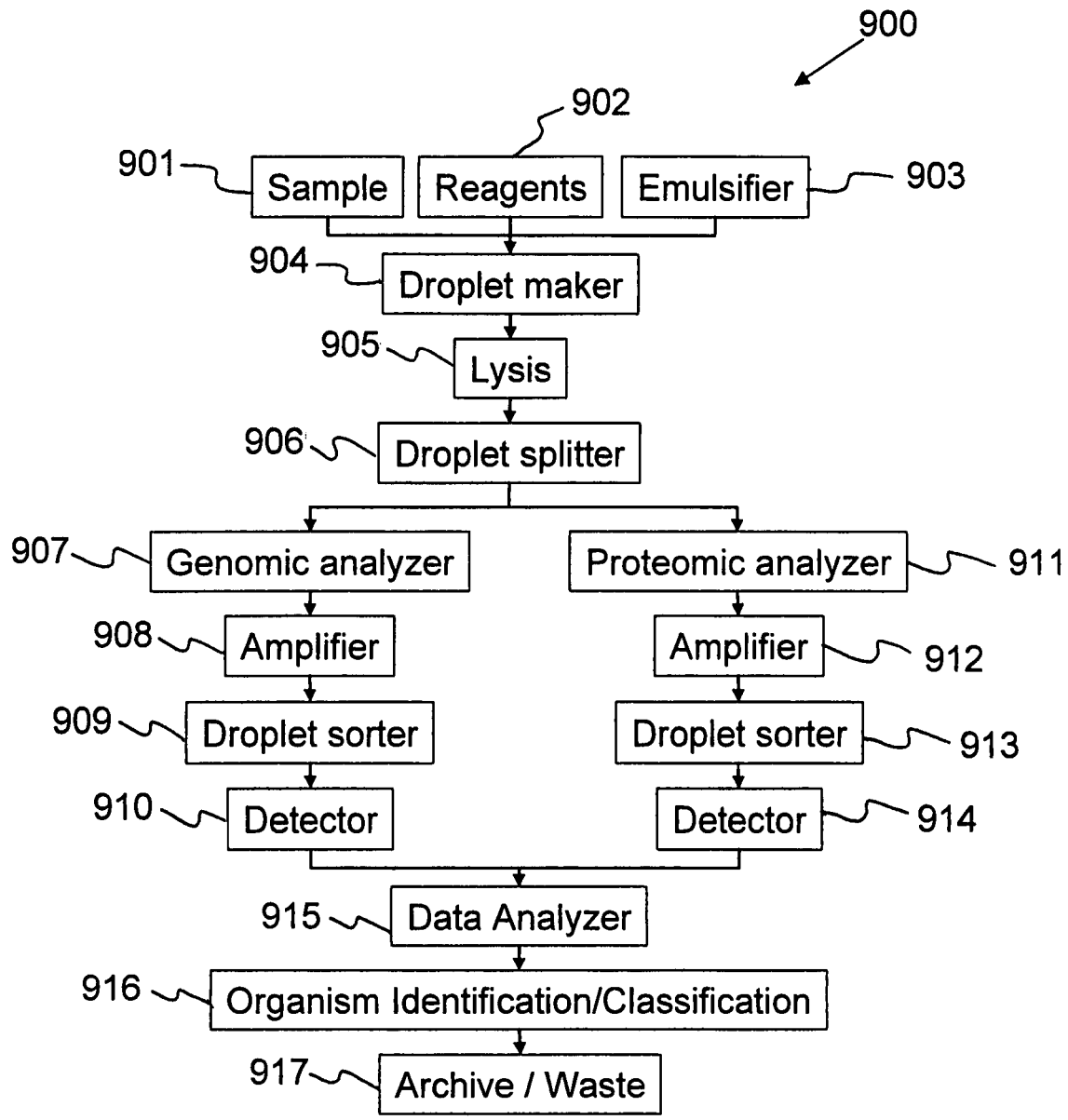
FIG. 9 illustrates a parallel genomic and proteomic analyzer system for identifying all of the unknown pathogenic or non-pathogenic organisms in a sample.

Referring now to FIG. 9, an embodiment of a system for parallel genomic and proteomic analysis of all of the unknown pathogenic or non-pathogenic organisms in a sample. The system is designated generally by the reference numeral 900. The system 900 identifies substantially all of the unknown pathogenic or non-pathogenic organisms in the sample 901.

As shown in FIG. 9, a sample 901 is directed into the system 900. The sample 901 contains unknown pathogenic or non-pathogenic organisms. The sample 901 is mixed with reagents 902 and an emulsifier 903. The reagents 902 may include those required for nucleic acid transcription and amplification and protein synthesis (translation) such as ribosomes, tRNAs, aminoacyl-tRNA synthetases, initiation, elongation and termination factors, amino acids, energy sources (ATP, GTP), energy regenerating systems (creatine phosphate, creatine phosphokinase, phosphoenol pyruvate, and pyruvate kinase), other co-factors (Mg2+, K+, etc.), primers, prokaryotic phage RNA polymerases and promoters (e.g., T7, T3, or SP6). The reagents can be added to the sample off-line or inline. Reagents can also be added through the use of fluidic junctions mixer.

As shown in FIG. 9, the emulsifier 903 is merged with the sample 901. The portion of the system 900 wherein the sample 901, the reagents 902, and the emulsifier 903 are injected forms a droplet maker 904. The droplet maker 904 creates droplets from the sample 901 wherein the droplets constitute sub-nanoliter volume reactors containing the organism sized particles. The droplets are created by forcing an aqueous sample stream and with immiscible liquid stream through an appropriately sized mechanical orifice in the droplet maker 904. This may be accomplished using microfluidic, microjet, inkjet, pin systems, or other ways of creating droplets. Merging an aqueous sample stream with immiscible liquid within the droplet maker 904 forms the droplets containing individual organisms.

A device 905 provides lysis of the organisms to release the nucleic acids. A droplet splitter 906 allows the microdroplets to be split into droplets to generate identical fractions of the sample for parallel analysis. After the splitting of the microdroplets, one set of microdroplets is sent to the genomic analyzer 907 and one set of microdroplets is sent to the proteomic analyzer 911.

One set of microdroplets is sent to the genomic analyzer 907. An amplifier 908 amplifies the sample 901. Amplification can be performed in highly parallel fluidic channels (stopped flow, flow-through) or using 1-D, 2-D or 3-D arrays. Signal amplification can also be incorporated as part of the target amplification step. Signal amplification relies on the multiplication of the response parameter, using for example enzymatic (e.g., luminescence), spectroscopic (e.g., SERS), or chemical (e.g., silver deposition on gold-nanoparticles) approaches.

A droplet sorter 909 sorts the droplets. Sorting identifies, and then collects the fraction of droplets containing a target organism that underwent successful amplification. Depending on the concentration of the organism in the sample, the size of the droplets and the efficiency of the amplification steps, many droplets may not have amplified. Sorting may reduce the burden on the detection system by presenting only a fraction of the total droplets for analysis. Sorting can be achieved using optical, hydrodynamic, and magnetic mechanisms or most likely a combination thereof. Sorting can be conducted within a fluidic channel. Sorting on a 1-D, 2-D or 3-D array can be achieved by assigning geometric coordinates to each category of droplet, followed by picking a sub-population of droplets for further analysis. Optical sorting can be based on measuring the spectroscopic properties of each droplet (e.g., luminescence, turbidity, light scattering, absorption, transmission, vibration, etc.). Optical sorting can be based on a direct spectroscopic measurement of the droplet and its contents. Alternatively, it can be an indirect measurement, whereby a specific indicator or probe was added to each droplet (e.g., a dsDNA intercalating fluorescence probe, labeled nano-particles to indicate successful PCR amplification, labeled antibody). Sorting can be non-invasive so as not to disrupt the microdroplets. Magnetic sorting can be achieved by incorporation of inert or labeled paramagnetic nano-particles to each droplet followed by application of an external magnetic field. Hydrodynamic sorting can be achieved using cytometry, diffusion, and focusing based approaches. A combination of pumps, valves and flow channels can be used to conduct high-throughput sorting of microdroplets.

A detector 910 provides detection of the organisms in the sample. The droplets may be split to provide aliquots of the amplified droplet material for delivery to a suite of detectors. The data analyzer 915 provides analysis. Analysis can be accomplished by performing informatics analysis of detector data to generate genomic and proteomic profiles for each organism sized particle in the original sample. Other physical analyses can also be performed (size, shape, pH, mobility, charge, viscosity, refractive index, kinetics, etc.). Information for each droplet is compiled, then analyzed to generate a comprehensive profile for each individual organism. The data from individual organisms can then be compiled to generate data representative of the entire population (i.e., the original sample). The module 916 provides identification/classification. An informatics and data analysis system for classification and identification of the all of the unknown pathogenic or non-pathogenic organisms in a sample is provided by the module 916. A fraction of the droplets may be discarded to waste or stored in a droplet archive as illustrated at 917.

The proteomic analyzer 911 provides proteomic analysis. The proteomic analysis may require protein synthesis by translation of RNA. Protein synthesis can be performed within microdroplets to identify gene products, conduct protein folding studies, and determine protein function. Protein synthesis can be achieved using in vitro translation (IVT) methods whereby the starting material can be RNA, circular DNA, linear DNA (plasmid) or PCR product. IVT can be performed in concurrently, or after nucleic acid amplification depending on the starting material.

An amplifier 912 amplifies the sample 901. Amplification can be performed in highly parallel fluidic channels (stopped flow, flow-through) or using 1-D, 2-D or 3-D arrays. Signal amplification can also be incorporated as part of the target amplification step. Signal amplification relies on the multiplication of the response parameter, using for example enzymatic (e.g., luminescence), spectroscopic (e.g., SERS), or chemical (e.g., silver deposition on gold-nanoparticles) approaches.

A droplet sorter 913 sorts the droplets. Sorting identifies, and then collects the fraction of droplets containing a target organism that underwent successful amplification. Sorting can be achieved using optical, hydrodynamic, and magnetic mechanisms or most likely a combination thereof. Sorting can be conducted within a fluidic channel. Sorting on a 1-D, 2-D or 3-D array can be achieved by assigning geometric coordinates to each category of droplet, followed by picking a sub-population of droplets for further analysis. Optical sorting can be based on measuring the spectroscopic properties of each droplet (e.g., luminescence, turbidity, light scattering, absorption, transmission, vibration etc.). Optical sorting can be based on a direct spectroscopic measurement of the droplet and its contents. Alternatively, it can be an indirect measurement, whereby a specific indicator or probe was added to each droplet (e.g., a dsDNA intercalating fluorescence probe, labeled nano-particles to indicate successful PCR amplification, labeled antibody). Sorting can be non-invasive so as not to disrupt the microdroplets. Magnetic sorting can be achieved by incorporation of inert or labeled paramagnetic nano-particles to each droplet followed by application of an external magnetic field. Hydrodynamic sorting can be achieved using cytometry, diffusion, and focusing based approaches. A combination of pumps, valves and flow channels can be used to conduct high-throughput sorting of microdroplets.

A detector 914 provides detection of the organisms in the sample and the organisms are identified and classified at 916.

The data analyzer 915 provides analysis. Analysis can be accomplished by performing informatics analysis of detector data to generate genomic and proteomic profiles for each organism sized particle in the original sample. Other physical analyses can also be performed (size, shape, pH, mobility, charge, viscosity, refractive index, kinetics, etc.). Information for each droplet is compiled, then analyzed to generate a comprehensive profile for each individual organism. The data from individual organisms can then be compiled to generate data representative of the entire population (i.e., the original sample). The module 916 provides identification/classification. An informatics and data analysis system for classification and identification of the all of the unknown pathogenic or non-pathogenic organisms in a sample is provided by the module 916. A fraction of the droplets may be discarded to waste or stored in a droplet archive as illustrated at 917.

Figure 10:
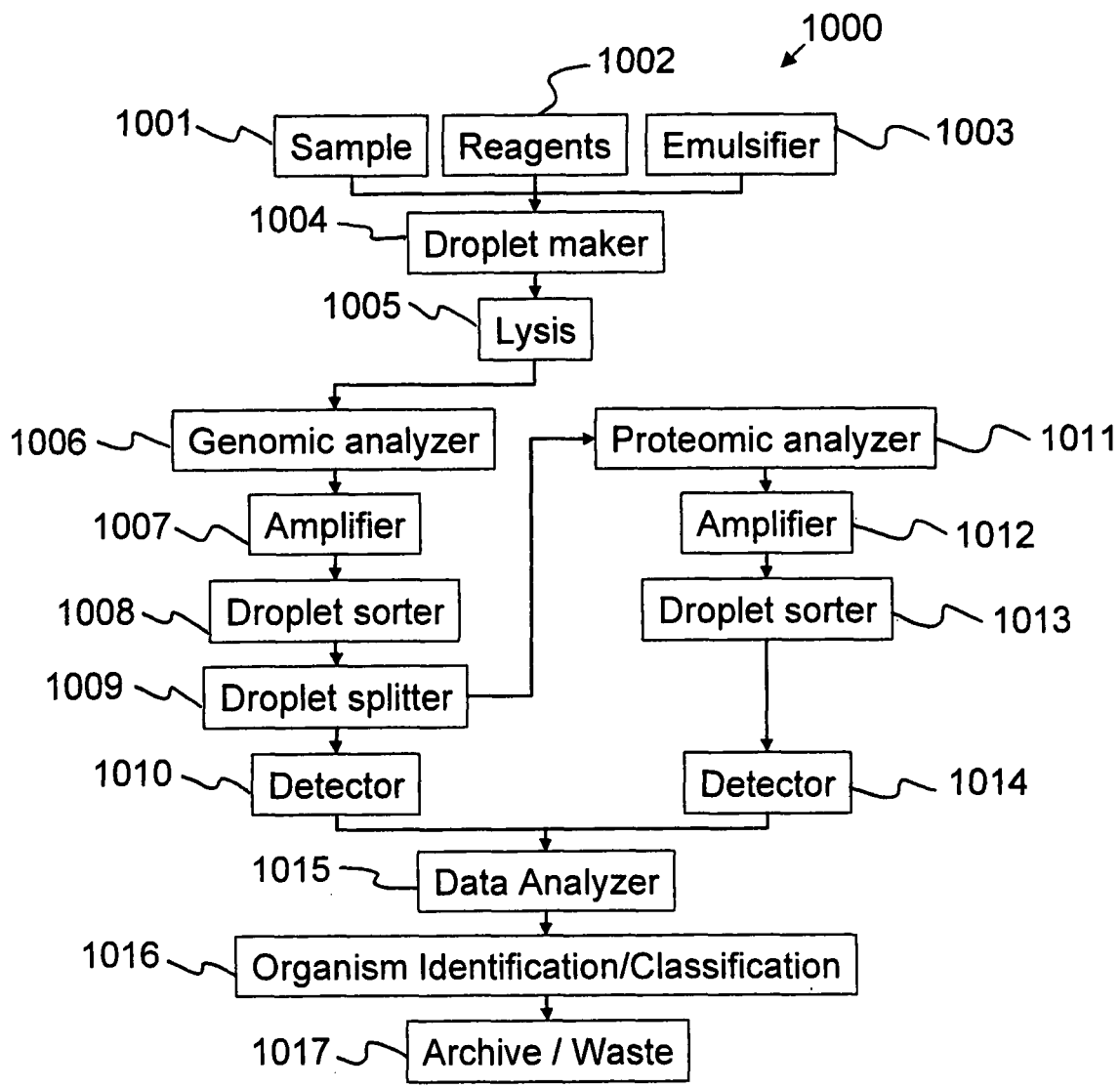
FIG. 10 illustrates a genomic and proteomic analyzer in a serial system for identifying all of the unknown pathogenic or non-pathogenic organisms in a sample.

Referring now to FIG. 10, an embodiment of a system for genomic and proteomic analysis of all of the unknown pathogenic or non-pathogenic organisms in a sample in series is shown. The system is designated generally by the reference numeral 1000. The system 1000 identifies substantially all of the unknown pathogenic or non-pathogenic organisms in the sample 1001.

As shown in FIG. 10, a sample 1001 is directed into the system 1000. The sample 1001 contains unknown pathogenic or non-pathogenic organisms. The sample 1001 is mixed with reagents 1002 and an emulsifier 1003. The reagents 1002 may be reagents required for nucleic acid amplification including primers, probes, and dNTPs, enzymes, buffer (Tris, potassium chloride, magnesium chloride). The reagents can be added to the sample off-line or inline. Reagents can also be added through the use of a fluidic junctions mixer.

As shown in FIG. 10, the emulsifier 1003 is merged with the sample 1001. The portion of the system 1000 wherein the sample 1001, the reagents 1002, and the emulsifier 1003 are injected forms a droplet maker 1004. The droplet maker 1004 creates droplets from the sample 1001 wherein the droplets constitute sub-nanoliter volume reactors containing the organism sized particles. The droplets are created by forcing an aqueous sample stream and with immiscible liquid stream through an appropriately sized mechanical orifice in the droplet maker 1004. This may be accomplished using microfluidic, microjet, inkjet, pin systems, or other ways of creating droplets. Merging an aqueous sample stream with immiscible liquid within the droplet maker 1004 forms the droplets containing individual organisms.

A device 1005 provides lysis of the organisms to release the nucleic acids. The microdroplets are sent to the genomic analyzer 1006. An amplifier 1007 amplifies the sample 1001. Amplification can be performed in highly parallel fluidic channels (stopped flow, flow-through) or using 1-D, 2-D or 3-D arrays. Signal amplification can also be incorporated as part of the target amplification step. Signal amplification relies on the multiplication of the response parameter, using for example enzymatic (e.g., luminescence), spectroscopic (e.g., SERS), or chemical (e.g., silver deposition on gold-nanoparticles) approaches.

A droplet sorter 1008 sorts the droplets. Sorting identifies, and then collects the fraction of droplets containing a target organism that underwent successful amplification. Depending on the concentration of the organism in the sample, the size of the droplets and the efficiency of the amplification steps, many droplets may not have amplified. Sorting may reduce the burden on the detection system by presenting only a fraction of the total droplets for analysis. Sorting can be achieved using optical, hydrodynamic, and magnetic mechanisms or most likely a combination thereof. Sorting can be conducted within a fluidic channel. Sorting on a 1-D, 2-D or 3-D array can be achieved by assigning geometric coordinates to each category of droplet, followed by picking a sub-population of droplets for further analysis. Optical sorting can be based on measuring the spectroscopic properties of each droplet (e.g., luminescence, turbidity, light scattering, absorption, transmission, vibration, etc.). Optical sorting can be based on a direct spectroscopic measurement of the droplet and its contents. Alternatively, it can be an indirect measurement, whereby a specific indicator or probe was added to each droplet (e.g., a dsDNA intercalating fluorescence probe, labeled nano-particles to indicate successful PCR amplification, labeled antibody). Sorting can be non-invasive so as not to disrupt the microdroplets. Magnetic sorting can be achieved by incorporation of inert or labeled paramagnetic nano-particles to each droplet followed by application of an external magnetic field. Hydrodynamic sorting can be achieved using cytometry, diffusion, and focusing based approaches. A combination of pumps, valves and flow channels can be used to conduct high-throughput sorting of microdroplets.

A droplet splitter 1009 allows the microdroplets to be split into droplets to generate identical fractions of the sample for analysis by detector 1010 and to be sent to the proteomic analyzer 1011. After the splitting of the microdroplets one set of microdroplets is sent to the proteomic analyzer 1011.

The proteomic analyzer 1011 provides proteomic analysis. The proteomic analysis may require protein synthesis. Protein synthesis can be performed within microdroplets to identify gene products, conduct protein folding studies, and determine protein function. Protein synthesis can be achieved using in vitro translation (IVT) methods whereby the starting material can be RNA, circular DNA, linear DNA (plasmid) or PCR product. IVT can be performed in concurrently, or after nucleic acid amplification depending on the starting material.

An amplifier 1012 amplifies the sample 1001. Amplification can be performed in highly parallel fluidic channels (stopped flow, flow-through) or using 1-D, 2-D or 3-D arrays. Signal amplification can also be incorporated as part of the target amplification step. Signal amplification relies on the multiplication of the response parameter, using for example enzymatic (e.g., luminescence), spectroscopic (e.g., SERS), or chemical (e.g., silver deposition on gold-nanoparticles) approaches.

A droplet sorter 1013 sorts the droplets. Sorting identifies, and then collects the fraction of droplets containing a target organism that underwent successful amplification. Sorting can be achieved using optical, hydrodynamic, and magnetic mechanisms or most likely a combination thereof. Sorting can be conducted within a fluidic channel. Sorting on a 1-D, 2-D or 3-D array can be achieved by assigning geometric coordinates to each category of droplet, followed by picking a sub-population of droplets for further analysis. Optical sorting can be based on measuring the spectroscopic properties of each droplet (e.g., luminescence, turbidity, light scattering, absorption, transmission, vibration, etc.). Optical sorting can be based on a direct spectroscopic measurement of the droplet and its contents. Alternatively, it can be an indirect measurement, whereby a specific indicator or probe was added to each droplet (e.g., a dsDNA intercalating fluorescence probe, labeled nano-particles to indicate successful PCR amplification, labeled antibody). Sorting can be non-invasive so as not to disrupt the microdroplets. Magnetic sorting can be achieved by incorporation of inert or labeled paramagnetic nano-particles to each droplet followed by application of an external magnetic field. Hydrodynamic sorting can be achieved using cytometry, diffusion, and focusing based approaches. A combination of pumps, valves and flow channels can be used to conduct high-throughput sorting of microdroplets. A detector 1014 provides detection of the organisms in the sample.

The data analyzer 1015 provides analysis. Analysis can be accomplished by performing informatics analysis of detector data to generate genomic and proteomic profiles for each organism sized particle in the original sample. Other physical analyses can also be performed (size, shape, pH, mobility, charge, viscosity, refractive index, kinetics, etc.). Information for each droplet is compiled, then analyzed to generate a comprehensive profile for each individual organism. The data from individual organisms can then be compiled to generate data representative of the entire population (i.e., the original sample). The module 1016 provides identification/classification. An informatics and data analysis system for classification and identification of the all of the unknown pathogenic or non-pathogenic organisms in a sample is provided by the module 1016. A fraction of the droplets may be discarded to waste or stored in a droplet archive as illustrated at 1017.

Figure 11:
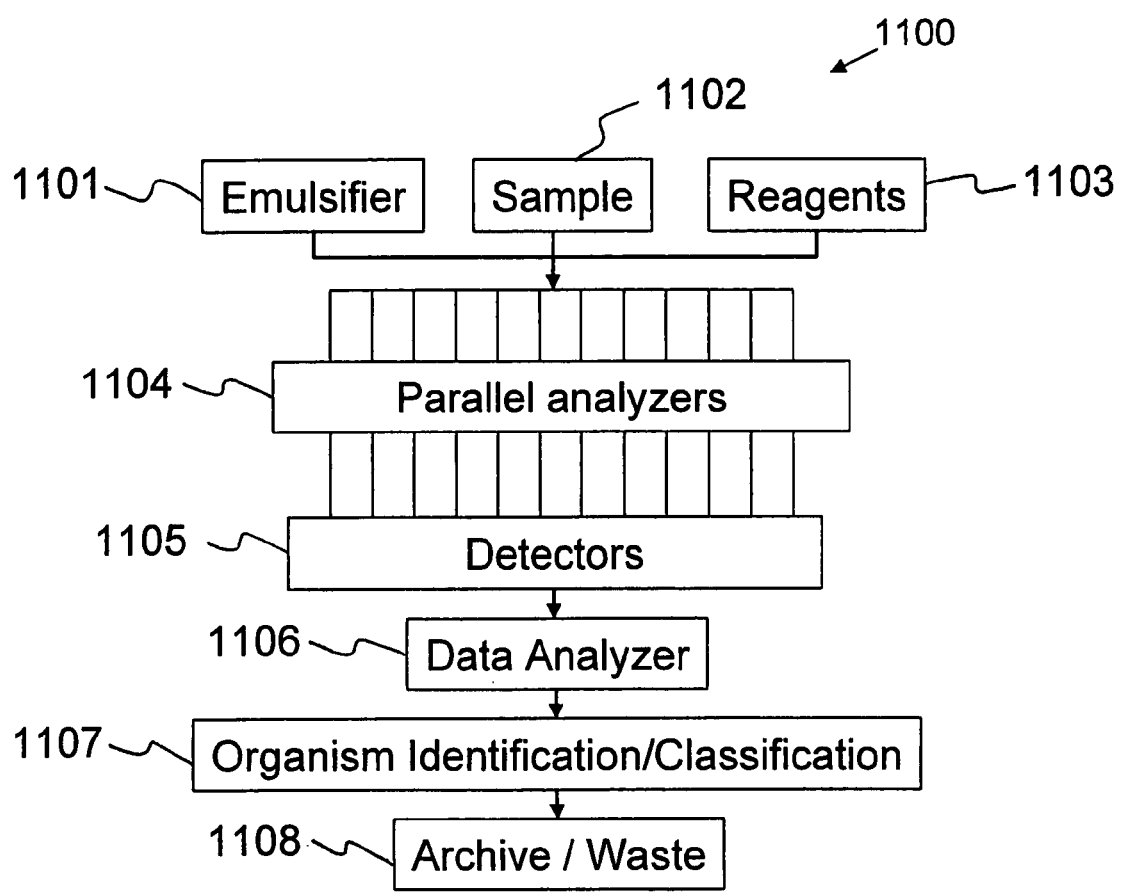
FIG. 11 illustrates parallel analyzers for identifying all of the unknown pathogenic or non-pathogenic organisms in a sample.

Referring now to FIG. 11 parallel analyzers for identifying all of the unknown pathogenic or non-pathogenic organisms in a sample are illustrated. The parallel analyzers are designated generally by the reference numeral 1100. The system 1100 identifies substantially all of the unknown pathogenic or non-pathogenic organisms in the sample 1101.

As shown in FIG. 11, a sample 1102 is directed into the system 1100. The sample 1102 contains unknown pathogenic or non-pathogenic organisms. The sample 1102 is mixed with reagents 1103 and an emulsifier 1101. The reagents 1103 may be reagents required for nucleic acid amplification and protein synthesis. The reagents can be added to the sample off-line or inline. Reagents can also be added using a fluidic junction mixer.

As shown in FIG. 11, the emulsifier 1101 and reagents 1103 merged with the sample 1102 and directed to the parallel analyzers 1104. The parallel analyzers 1104 can be Genomic Analyzers or Proteomic Analyzers or a combination of Genomic Analyzers and Proteomic Analyzers.

Detectors 1105 provide detection of the organisms in the sample. The data analyzer 1106 provides analysis. Analysis can be accomplished by performing informatics analysis of detector data to generate genomic and proteomic profiles for each organism sized particle in the original sample. Other physical analyses can also be performed (size, shape, pH, mobility, charge, viscosity, refractive index, kinetics, etc.). Information for each droplet is compiled, then analyzed to generate a comprehensive profile for each individual organism. The data from individual organisms can then be compiled to generate data representative of the entire population (i.e., the original sample). The module 1107 provides identification/classification. An informatics and data analysis system for classification and identification of the all of the unknown pathogenic or non-pathogenic organisms in a sample is provided by the module 1107. A fraction of the droplets may be discarded to waste or stored in a droplet archive as illustrated at 1108.

Other apparatus for performing the method(s) of the present invention are described and illustrated in U.S. patent application Ser. No. 11/650,363 filed Jan. 4, 2007 by Neil Reginald Beer, Benjamin J. Hindson, Billy W. Colston, Jr., and Joseph Patrick Fitch titled, "Sorting, Amplification, Detection, and Identification of Nucleic Acid Subsequences in a Complex Mixture." U.S. patent application Ser. No. 11/650,363 titled, "Sorting, Amplification, Detection, and Identification of Nucleic Acid Subsequences in a Complex Mixture" filed Jan. 4, 2007 by Neil Reginald Beer, Benjamin J. Hindson, Billy W. Colston, Jr., and Joseph Patrick Fitch is incorporated herein by this reference.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for identifying pathogenic and non-pathogenic organisms in a sample, comprising:

a sample preparation means for preparing the sample, said
sample preparation means including
reagents and
an emulsifier, and
means for mixing said reagents and said emulsifier, and
droplet maker means, said droplet maker means including
an orifice wherein said droplet maker means forces the
sample with the organisms in the sample and said
reagents mixed with said emulsifier through said orifice
to produce microdroplets with the sample with the
pathogenic and non-pathogenic organisms in said
microdroplets;
an amplifier for amplifying the pathogenic and non-pathogenic organisms in the sample in said microdroplets,
said amplifer connected to said droplet maker;
a sorter for sorting said microdroplets, said sorter connected to said amplifier;
an analyzer for analyzing said microdroplets, said analyzer
connected to said sorter; and
a system for classifying and identifying the pathogenic and
non-pathogenic organisms in the sample in said microdroplets, said system for classifying and identifying the
organisms connected to said analyzer.

2. An apparatus for identifying pathogenic and non-pathogenic organisms in a sample, comprising:
sample preparation means for preparing the sample, said
sample preparation means including
reagents and
an emulsifier, and
means for mixing said reagents and said emulsifier, and
droplet maker means, said droplet maker means including
an orifice wherein said droplet maker means forces the
sample with the organisms in the sample and said
reagents mixed with said emulsifier through said orifice
to produce microdroplets with the sample with the
pathogenic and non-pathogenic organisms in said
microdroplets;
amplifier means for amplifying the pathogenic and non-pathogenic organisms in the sample in said microdroplets connected to said droplet maker, wherein said amplifier means includes PCR amplification means for
amplifying the pathogenic and non-pathogenic organisms in the sample in said microdroplets;
a sorter for sorting said microdroplets, said sorter connected to said amplifier;
an analyzer for analyzing said microdroplets, said analyzer
connected to said sorter; and
a system for classifying and identifying the pathogenic and
non-pathogenic organisms in the sample in said microdroplets, said system for classifying and identifying the
organisms connected to said analyzer.

3. An apparatus for identifying pathogenic and non-pathogenic organisms in a sample, comprising:
sample preparation means for preparing the sample, said
sample preparation means including
reagents and
an emulsifier, and
means for mixing said reagents and said emulsifier, and
droplet maker means, said droplet maker means including
an orifice wherein said droplet maker means forces the
sample with the organisms in the sample and said
reagents mixed with said emulsifier through said orifice
to produce microdroplets with the sample with the
pathogenic and non-pathogenic organisms in said
microdroplets;
an amplifier for amplifying the pathogenic and non-pathogenic organisms in the sample in said microdroplets,
said amplifier connected to said droplet maker;
sorter means for sorting said microdroplets, said sorter
connected to said amplifier, wherein said sorter means
comprises an optical sorter, a hydrodynamic sorter, or a
magnetic sorter or any combination of an optical sorter,
a hydrodynamic sorter, or a magnetic sorter;
an analyzer for analyzing said microdroplets, said analyzer
connected to said sorter; and
a system for classifying and identifying the pathogenic and
non-pathogenic organisms in the sample in said microdroplets, said system for classifying and identifying the
organisms connected to said analyzer.

4. An apparatus for identifying pathogenic and non-pathogenic organisms in a sample, comprising:
a sample preparation system for preparing the sample, said
sample preparation system including
reagents and
an emulsifier, and
a droplet maker, said droplet maker including an orifice
wherein said droplet maker forces the sample with the
organisms in the sample and said reagents mixed with
said emulsifier through said orifice to produce microdroplets with the sample with the pathogenic and non-pathogenic organisms in said microdroplets;
an amplifier for amplifying the pathogenic and non-pathogenic organisms in the sample in said microdroplets,
said amplifier connected to said droplet maker;
a sorter for sorting said microdroplets, said sorter connected to said amplifier;
an analyzer for analyzing said microdroplets, said analyzer
connected to said sorter; and
a system for classifying and identifying the pathogenic and
non-pathogenic organisms in the sample in said microdroplets, said system for classifying and identifying the
organisms connected to said analyzer, wherein said system for classifying and identifying the pathogenic and
non-pathogenic organisms in the sample in said microdroplets comprises a sequencer.

5. An apparatus for identifying pathogenic and non-pathogenic organisms in a sample, comprising:
a sample preparation system for preparing the sample, said
sample preparation system including
reagents and
an emulsifier, and
a droplet maker, said droplet maker including an orifice
wherein said droplet maker forces the sample with the
organisms in the sample and said reagents mixed with
said emulsifier through said orifice to produce microdroplets with the sample with the pathogenic and non-pathogenic organisms in said microdroplets;
an amplifier for amplifying the pathogenic and non-pathogenic organisms in the sample in said microdroplets,
said amplifier connected to said droplet maker;
a sorter for sorting said microdroplets, said sorter connected to said amplifier;
an analyzer for analyzing said microdroplets, said analyzer
connected to said sorter, wherein said analyzer for analyzing said microdroplets is a parallel analyzer; and
a system for classifying and identifying the pathogenic and
non-pathogenic organisms in the sample in said microdroplets, said system for classifying and identifying the
organisms connected to said analyzer.

* * * * *